United States Patent
Baldeschwieler et al.

[11] Patent Number: 5,847,105
[45] Date of Patent: Dec. 8, 1998

[54] METHODS FOR PERFORMING MULTIPLE SEQUENTIAL REACTIONS ON A MATRIX

[75] Inventors: John D. Baldeschwieler, Pasadena; Ronald C. Gamble, Altadena; Thomas P. Theriault, Manhattan Beach, all of Calif.

[73] Assignee: California Institute of Technology, Pasadena, Calif.

[21] Appl. No.: 910,727

[22] Filed: Aug. 13, 1997

Related U.S. Application Data

[63] Continuation of Ser. No. 457,431, Jun. 1, 1995, abandoned, which is a continuation of Ser. No. 213,857, Mar. 16, 1994.

[51] Int. Cl.⁶ .................................................. C07H 21/00
[52] U.S. Cl. .......................... 536/25.3; 435/6; 436/501; 935/77; 935/78
[58] Field of Search .............................. 435/6, 91.1, 810; 436/501; 536/22.1, 23.1, 24.1, 24.3, 24.33, 25.3; 935/77, 78

[56] References Cited

U.S. PATENT DOCUMENTS

| | | | |
|---|---|---|---|
| 4,562,157 | 12/1985 | Lowe et al. | 435/291 |
| 4,866,166 | 9/1989 | Wigler | 536/27 |
| 5,073,495 | 12/1991 | Anderson | 435/284 |
| 5,143,854 | 9/1992 | Pirrung et al. | 436/518 |
| 5,200,051 | 4/1993 | Cozzette et al. | 204/403 |
| 5,202,231 | 4/1993 | Drmanac et al. | 435/6 |
| 5,202,418 | 4/1993 | Lebl et al. | 530/334 |
| 5,474,796 | 12/1995 | Brennan | 427/2.13 |

FOREIGN PATENT DOCUMENTS

| | | |
|---|---|---|
| 2090485 | 8/1991 | Canada . |
| 2080920 | 10/1991 | Canada . |
| 2086672 | 1/1992 | Canada . |
| 0 138 075 | 4/1985 | European Pat. Off. . |
| 0 260 965 | 3/1988 | European Pat. Off. . |
| 0 392 546 A2 | 10/1990 | European Pat. Off. . |
| WO 87/02133 | 4/1987 | WIPO . |
| WO 88/02019 | 3/1988 | WIPO . |
| WO 89/10977 | 11/1989 | WIPO . |
| WO 90/00626 | 1/1990 | WIPO . |
| WO 90/03382 | 4/1990 | WIPO . |
| WO 92/10588 | 6/1992 | WIPO . |
| WO 93/04204 | 3/1993 | WIPO . |
| WO 93/09668 | 5/1993 | WIPO . |
| WO 93/17126 | 9/1993 | WIPO . |
| WO 93/22480 | 11/1993 | WIPO . |
| WO 94/27719 | 12/1994 | WIPO . |
| WO 95/04160 | 2/1995 | WIPO . |

OTHER PUBLICATIONS

Lipshutz (1993) Journal of Biomolecular Structure & Dynamics 11:637–653.
Southern et al. (1992) Genomics 13:1008–1017.
Maskos et al. (1992) Nucleic Acids Research 20:1679–1684.
Southern (1975) J. Mol. Biol. 98:503–517.
Brennan, "Sequencing by Hybridization: Methods to Generate Large Arrays of Oligonucleotides", *Human Genome 1991–92 Program Report*, published by the United Stated Department of Energy, Jun. 1992.

*Primary Examiner*—Ardin H. Marschel
*Attorney, Agent, or Firm*—Swanson & Bratschun LLC

[57] ABSTRACT

A method and apparatus are provided for preparing a substrate upon which is located microdrop-sized loci at which chemical compounds are synthesized or diagnostic tests are conducted. The loci are formed by applying microdrops from a dispenser from which a microdrop is pulse fed onto the surface of the substrate.

18 Claims, 2 Drawing Sheets

1

METHODS FOR PERFORMING MULTIPLE SEQUENTIAL REACTIONS ON A MATRIX

RELATED APPLICATIONS

This application is a file wrapper continuation of U.S. application Ser. No. 08/457,431, filed Jun. 1, 1995, now abandoned, which is a continuation of U.S. application Ser. No. 08/213,857, filed Mar. 16, 1994.

FIELD OF THE INVENTION

The present invention is directed to a method and apparatus for performing sequential reactions on a plurality of sites on a matrix using noncontiguous microdrop-sized loci. The apparatus and method are useful for performing a test or synthesis involving sequential steps such as DNA sequencing, DNA diagnostics, oligonucleotide and peptide synthesis, screening tests for target DNA, RNA or polypeptides, synthesis of diverse molecules, DNA separation technology whereby DNA binds to target molecules, preparation of polysaccharides, methods for making complementary oligonucleotides, and any other test, sequencing or synthetic method utilizing a sequence of steps at a locus. An advantage or improvement can be obtained by providing loci so that combinations of different reactions may be conducted on the same matrix.

BACKGROUND OF THE INVENTION

Methods are known for performing a plurality of sequential tests or reactions at loci on a matrix by attachment of molecules to a solid phase. Typically, a solid phase is prepared having a free functional group such as a hydroxy group, amino group, etc. and linking groups are attached to the surface by way of covalent linkages. These linkers serve as "handles" to which molecules may be attached for sequential synthesis of such linear molecules as polypeptides and polynucleotides. A disadvantage of such solid state synthesis is that the entire substrate or a large portion of the substrate must be exposed to a single reagent, such as the reagent which is the next molecule to be attached to the substrate, a rinsing agent or a deprotecting agent.

In some instances, locations on the substrate can be selectively treated if the reaction to be conducted is photolytic in nature, so masks may be prepared to expose selected areas to the activating radiation. However, an obvious disadvantage is that reactions must be devised which can be conducted by photolytic activation and different masks must be used to shield portions of the substrate at which the reaction is undesired.

The present invention provides a method whereby reactions may be conducted on noncontiguous microdrop-sized loci on a substrate. Since the reagents according to the present invention are in liquid form, virtually any chemical reaction which may be conducted in solution or suspension may be performed.

It is therefore an object of the present invention to provide a method and apparatus for performing a plurality of sequential reactions on a substrate whereby the reactions are conducted on microdrop-sized loci and, if desired, a different sequence of reactions may be conducted at each locus.

Furthermore, an object of the present invention is to provide a method and apparatus for conducting a plurality of sequential reactions on a matrix using liquid reagents whereby the chemical reactions may be performed in solution or suspension.

These and other objects of the invention will be apparent from the following description, the appended claims and from the practice of the invention as described herein.

SUMMARY OF THE INVENTION

The present invention provides a method and apparatus for performing a plurality of chemical reactions at different sites on a substrate wherein the same or different tests, sequencing or synthetic reactions may be conducted at the loci. The invention provides a substrate having a surface which has chemical moieties that are reactive with reagents that are dispensed from a microdrop dispensing device. These reagents may be molecules that become attached to the surface in the microdrop loci to which they are dispensed, as in the application of activated nucleic acid phosphoramidites, or the reagents may modify the surface in the microdrop loci for subsequent chemical reactions, as in the deprotection of the 5' hydroxyl group during the synthesis of oligonucleotides. In the case of delivery of reagents that become attached to the surface, the invention provides a substrate having a surface to which a first reagent can be attached by dispensing microdrops of the reagent in liquid form onto the substrate. The dispenser is displaced relative to the surface and at least one microdrop is applied thereto containing the same or a different reagent. By repeating this using the same or a different first reagent in liquid form, a plurality of loci on the surface may be prepared wherein the reagents covalently attach at microdrop-sized loci wherein the boundaries of each locus are not contiguous to any adjacent locus. The surface may then be washed to remove unattached reagent. If needed, the entire surface may be treated, or alternatively, a selected subset of loci may be treated, with deprotecting reagents to expose reactive sites of the molecules attached to the surface. The deprotecting reagent may also be dispensed from the device. Then one or more microdrops containing a second reagent in liquid form may be dispensed at selected loci on the substrate surface, whereby the second reagent is selected to react with the molecules already attached to the matrix. The dispenser is again displaced relative to the surface to apply the second reagent at different loci using the same or a different second reagent which reacts with the respective attached molecules. Again, the entire surface will be washed to remove unreacted second reagents. Then the entire surface or selected subsets of loci may be treated with deprotecting agents, and this process may be repeated.

In the case of delivery of reagents that modify the reactivity of the surface, the invention provides a substrate having a surface to which the reagent is applied by dispensing one or more microdrops onto the substrate. The dispenser is displaced relative to the surface and one or more microdrops are applied thereto. This process may continue until the desired set of microdrop-sized loci have been modified by the application of reagent. The surface may then be washed to remove excess reagent. The entire surface or a selected subset of loci, may be treated with a reagent that becomes attached to the loci modified by the microdrop dispensed reagent, or alternatively a reagent may be applied that becomes attached to the surface except at the loci that were previously modified by the microdrop dispensed reagent. If the reagents that become attached to the surface contain chemical moieties that can be modified by the microdrop dispensed reagent, the process may be repeated such that the same or different loci are modified by the microdrop dispensed reagent and then reacted with a reagent or reagents that become attached to the modified loci until the desired compounds have been synthesized on the substrate.

It will also be recognized that a combination of the above strategies may be employed wherein both the reagents that become attached to the surface in microdrop loci and reagents that modify the surface in microdrop loci are dispensed by the microdrop dispensing device.

Upon completing the desired number of sequential steps at the loci on the substrate, the compounds may be removed selectively or non-selectively, if desired, from the substrate using cleavage reagents which remove compounds bound through linking groups to solid substrates. Cleavage agents include enzymatic or other chemical agents, which may also be dispensed as microdrops at selected loci. It will be appreciated, for example, in the case of diagnostic methods, isolation of the final compound located in each of the loci is not important, therefore cleavage of the compound from the substrate is an optional step.

In some circumstances, it may be desirable to analyze the molecules directly upon cleavage from the substrate by such techniques as mass spectrometry. In such instances, it is desirable to provide a linker (the moiety through which the molecule in question is attached to the substrate) which is cleavable by electron beam, laser, or other energy source so that molecules at a locus may be selectively cleaved from the substrate. This is particularly advantageous for analyzing the molecules by mass spectrometry, whereby the laser or electron beam cleaves the molecules from the substrate, ionization occurs, and the ions are accelerated into a mass spectrometer.

The substrate may be a solid, such as glass, prepared to receive linkers attached to the surface. Porous substrates, such as paper or synthetic filters may be used, as well as filters (such as those sold by Nucleopore) having straight, parallel micropores. In such a microporous substrate, the reactions may take place within the pores, thus amplifying the potential signal at the locus.

It will also be recognized that the present invention provides a method for determining the presence of an analyte in a sample by contacting the sample with a device prepared according to the present invention having a plurality of microdrop-sized loci of covalently attached reagents whereby the analyte binds to at least some of the reagents. Detection of the loci at which binding occurs may be performed by conventional methods such as fluorescence, chemiluminescence, calorimetric detection, radioactive label detection, and the like.

The present invention also provides a method for delivery of microdrops to the substrate that relies on positioning the substrate such that the separation between the dispenser and substrate is less than the separation required for free droplet formation. In this configuration, the liquid column emerging from the nozzle due to the applied pressure pulse impacts upon the substrate before a droplet forms (i.e., a column of liquid stretches between the nozzle and substrate). The impact upon the substrate alters the flow of liquid from the nozzle such that a much smaller amount of liquid is ultimately delivered to the substrate as compared to the case where distinct droplets are formed. This method allows for much closer spacing of loci on the substrate and higher positional precision for the placement of loci.

DESCRIPTION OF PREFERRED EMBODIMENTS

Figure 1A:
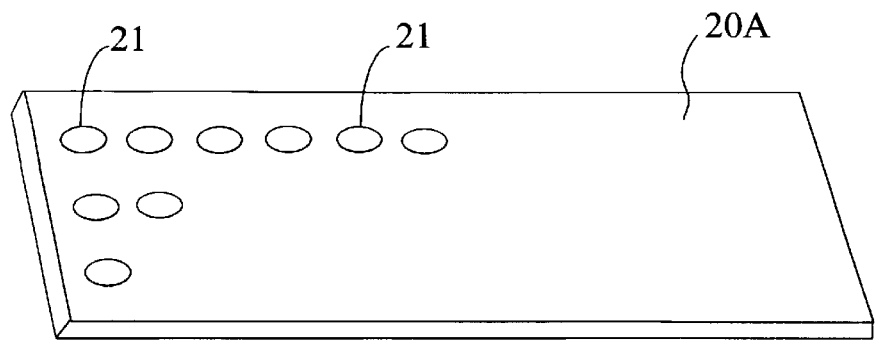
FIG. 1A shows a substrate having microdrop sized loci on one surface.

The present invention provides a method for performing a plurality of sequential reactions on a substrate. The surface of the substrate contains chemical moieties that react with reagents that are dispensed from a microdrop dispensing device. The reagents may be molecules that become attached to the surface of the substrate in the microdrop loci to which they are dispensed or the reagents may modify the surface of the substrate to facilitate the formation of a covalent bond between the surface and a second reagent. In the latter case, the entire surface or a selected subset of loci may then be treated with a second reagent that becomes covalently attached to the loci modified by the first reagent. If only a selected subset of loci are treated with the second reagent, this step may be repeated with a third reagent that becomes attached to another subset of loci modified by the first reagent.

The present invention may be utilized to prepare, for example, molecules such as peptides. In a preferred embodiment a linker molecule is provided as the first reagent whereby one end of the linker will be attached to the substrate surface. The other end of the linker will be adapted to form a linkage with the carboxy terminal of an amino acid or peptide, to form, for example, an amide or ester linkage. This end of the linker may be initially chemically protected by protecting groups such as t-butoxycarbonyl groups (t-BOC) or other protecting groups known in the peptide synthesis art. By application of a second reagent onto the locus which removes a protecting group, such as acid solution, the protecting group may be removed. The next reagent applied at each locus would then be an amino terminal-protected and side-chain protected amino acid or polypeptide, preferably having an activated C-terminal group for linking the C-terminal to the end of the linker. This process may be repeated with the same or different amino acids or peptides at each of the microdrop loci until the substrate includes the peptides of desired sequences and lengths. Thereafter, the protective groups are removed from some or all of the peptides, as desired. The deprotection may be achieved using a common deprotection agent, which removes the protecting groups on side chains and the amino ends simultaneously, as is known in the peptide synthesis art. The peptides may be cleaved from the linker using methods known to those of ordinary skill in the peptide synthesis art which cleave peptides from a solid support as, for example, used in the Merrifield synthesis technique.

It will be realized that a particular advantage of this method is that, by keeping a record of the reagents utilized at each of the microdrop sized loci, peptides of different lengths and sequences may be made concurrently on the same substrate. Such peptides may have a variety of uses including, but not limited to, screening for biological activity whereby the respective peptide sequences at each locus is exposed to a labeled or unlabeled peptide receptor, such as an antibody, a cell receptor, or any other variety of receptor.

The method according to the present invention may also be utilized to prepare oligonucleotides by sequentially dispensing through the microdrop dispenser protected nucleic acids. These may be added sequentially at each locus using the same or different nucleic acids or polynucleotides. Preferably, the 3'-end of the oligonucleotide will be attached to the linker molecule and the oligonucleotide will be synthesized from the 3' end to the 5' end using known techniques for oligonucleotide synthesis. The protecting groups are preferably those known in the oligonucleotide synthesis art. The oligonucleotide may be utilized, for example, for hybridization with an unknown oligonucleotide to determine the sequence of the unknown oligonucleotide.

An oligonucleotide synthesized at one locus may be utilized to synthesize its complementary oligonucleotide by using DNA polymerase. Preferably, the locus will comprise straight pores in a porous substrate. The complementary oligonucleotide may then be removed by washing a denaturing agent through the pores onto a new substrate, thereby resulting in one substrate (the original porous substrate) containing the oligonucleotides which were originally synthesized, and another substrate containing their complements.

An array of synthesized oligonucleotides may be used to generate an array of complementary oligonucleotides by using pre-synthesized oligonucleotides, optionally containing a reactive chemical moiety such as a spacer with a primary amine that attaches the the phosphate chain. In this embodiment, the pre-synthesized oligonucleotides are hybridized to the array of oligonucleotide prepared with the microdrop dispenser. The localized complementary oligonucleotides are preferably removed from the synthesized array in denaturing conditions and washed onto a second substrate. This second substrate is preferably a material such as a nylon or nitrocellulose membrane, or surface with amino reactive linkers, where the oligonucleotides become immobilized. Preferably a flow system onto the second substrate is utilized such that the net flow is essentially perpendicular to the original substrate so that the the complementary oligonucleotides in adjacent loci do not intermingle. This may also be accomplished by employing an electric field that is perpendicular to the original substrate such that the complementary oligonucleotides elecrophorese onto the second substrate.

In yet another embodiment of the present invention the substrate to which oligonucleotides are attached may be used as a tool in gene therapy whereby mutations maybe identified in a genome. For example, oligos complementary to fragments of the known sequence of the normal gene may be attached to the substrate. Digestion of a single strand of the gene from the subject in question and contact with the substrate containing complementary oligo sequences may reveal oligos to which there is binding, thereby indicating the presence or absence of fragments in the subject's genome.

The substrate containing oligos may also be used to identify DNA in samples from the environment to detect, for example, the presence or absence of certain species, in the case where the DNA sequences are known, or to determine the presence of DNA fragments which anneal to the substrate in the case where the DNA sequences are unknown. The oligonucleotides may be thereafter amplified by PCR amplification technology.

If the substrate is a porous filter, membrane or other material which can be cut, the substrate may be divided into portions containing one locus (or a plurality of loci having identical or different molecules). These portions may be placed in microtiter wells for diagnostic or therapeutic tests whereby each well is separately treated with a sample.

One application of the present invention is to prepare an array of oligonucleotides for the sequencing of DNA by hybridization. The basis for this method is that a given sequence can be constructed from the knowledge of its constitutive set of overlapping sequence segments, provided there is a certain degree of uniqueness among these segments. The set of overlapping sequence segments of length n can be obtained by hybridization of the unknown DNA to a set of n-mer oligonucleotides which represent all $4^n$ possible sequences. The advantages of sequencing by hybridization include faster sequence determination, lower cost, ease of automation and higher reliability (as compared to a single sequence reading from a gel). For an array of oligonucleotides of length n it is possible to determine the average length of DNA fragment that can be unambiguously sequenced. Although difficulties can arise when a fragment of length n−1 appears in the sequence more than once, nevertheless, statistical analyses have shown sequencing by hybridization to be a feasible method. The relationship between the length of oligonucleotides and the length of the average resolvable sequence has been determined. Typical numbers are shown in Table 1. For example, an array of all 65536 octamers can be used in the sequencing of short, 100 to 200 base pair fragments.

TABLE 1

Length of possible sequence determination versus the length of oligonucleotides used for hybridization.

| Length of oligonucleotide | Length of sequence identifiable* |
|---|---|
| 7 | 80 |
| 8 | 180 |
| 9 | 260 |
| 10 | 560 |
| 11 | 1300 |
| 12 | 2450 |

*These numbers represent the length for which sequence reconstruction will be possible in 95% of all cases.

Furthermore, it has been shown that inclusion of a random content fixed length gap in the oligonucleotides of the array can be used to achieve higher lengths of sequence resolution. The combination of an array of all $4^8$ octamers and an array of all $4^8$ octamers with a random nucleotide inserted in the middle of the octamer has nearly the same resolving power as an array of all $4^9$ nonamers, even though the nonamer array is twice as large.

The preferred ink jet device utilized to deliver the microdrops generates addresses less than 100 microns across, and address sizes as small as 10 microns are attainable. A primary advantage to use of the ink jet is that standard methods for oligonucleotide synthesis that have been optimized for extremely high yields can be employed.

By employing a multiple jet device the synthesis of complete arrays of oligonucleotides can proceed four times faster and with less material than can be accomplished by performing only addressable deprotection. The simplest design to accomplish this is a five jet system, one jet each for the four phosphoramidite reagents and one jet for the activating tetrazole solution. The operation of this device is directly analogous to the operation of color ink jet printers. In every coupling cycle, for each address on the array a number is assigned to indicate the correct synthon to be added. During the reagent delivery process, the stage rasters through the addresses of the array. Tetrazole is first applied to the substrate. At each address an additional offset motion is applied to bring the correct phosphoramidite jet (A, C, G or T) in line. One or more droplets of the phosphoramidite are then dispersed. Subsequent to this a second offset motion is employed to bring the tetrazole jet in line with the address. After dispersal of the tetrazole reagent, the stage can raster to the next address for a new delivery cycle. The software for the advanced device is very similar to the control software described in the examples with a modification that a 'color' bitmap is used to represent the array. The four phosphoramidite reagents are each assigned to a specific color. During the raster through the array for delivery, the color at each pixel in the bitmap is translated to the offset motion to bring the correct reagent in line with the address. The tetrazole jet fires at every address position.

The tetraethylene glycol linker is useful for single hybridization with oligonucleotides. Low non-specific binding has been observed. Longer polymers of ethylene glycol may be utilized, as well as modified phosphodiesters. Phosphoramidite reagents are commercially available that may be polymerized in a stepwise manner to yield dimethoxytrityl-capped linkers of virtually any length desired. Since this linkage is ultimately a phosphodiester with phosphates spaced by alkyl chains of only a few carbons, it will have similar hydrophilicity to standard DNA. Further, since the linker is negatively charged at neutral pH, lower non-specific binding of DNA to the substrate is expected.

To address the question of coupling efficiency and thus the sequence fidelity in the synthesized arrays the preferred method is to synthesize large arrays, where all addresses contain the same sequence, and perform Maxam-Gilbert sequencing directly on the substrate region that contains the array. Prior to the start of sequencing the array may be end-labeled with $^{32}$ P phosphate.

The sequencing by hybridization may require either larger arrays, for example the undecamer array, or arrays that have been optimized to obtain more information from a set of hybridization tests. For such large arrays, the complete set of undecamers has 4.2 million members, therefore small address and guard regions are advantageous. With 100 micron addresses and 50 micron guard regions, parameters that are within the capacity of examples disclosed herein, the entire undecamer array would occupy an area of 10.5×10.5 square inches.

In yet another embodiment the microdrops may be used to synthesize polysaccharides using the monosaccharides as building blocks. However, it will be readily apparent that many other types of polymeric materials may be made according to the present invention whereby the same or different polymers maybe be constructed at each locus on the substrate.

In a particularly advantageous use of the present invention, small molecules may be made whereby the molecules may be built sequentially using reagents in a multi-step synthesis. These need not be polymeric molecules where there is a repetitive unit. Since different reagents may be applied to one or more of the loci on the substrate, there is an advantageous diversity of structures that can be attained by the multiple and concurrent synthesis technology according to the present invention. The target compounds may be contemporaneously, but separately synthesized on the substrate to generate an ensemble of compounds which may or may not be structurally related. Each step of the synthesis which occurs at each locus should involve soluble reagents, and should occur at a reasonable yield at typical ambient temperatures, since most or all of the sites on the substrate will be essentially isothermal. For example, a benzodiazepine may be prepared from an amino acid bound to the substrate by the carbon terminus. Treatment with a microdrop containing 2-aminobenzophenone imine forms a substrate-bound imine and then treatment with TFA (trifluoro acetic acid) generates a benzodiazepine. By using different amino acids and different aminobenzophenones, an array of different benzodiazepines maybe made in this manner.

Reference will be made now to the various figures which further describe the preferred modes for practicing the invention.

Figure 1B:
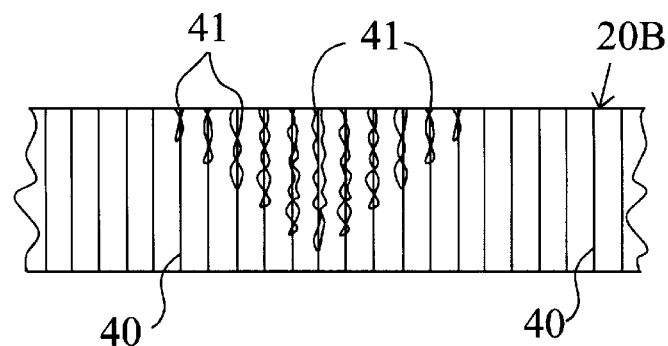
FIG. 1B shows the cross-section of a microporous substrate with straight, parallel micropores having a microdrop-sized locus containing attached molecules.

Referring now to the figures, in FIG. 1A there is shown a substrate 20A having on one surface thereof the microdrops 21 which define each locus at which the chemical synthesis or diagnostic reaction may take place according to the present invention. Since each microdrop is discrete and noncontiguous with adjacent microdrops, reactions may be conducted at each microdrop which are independent of reactions at other microdrops. In FIG. 1B, there is shown a microporous substrate 20B having straight, parallel micropores 40. The growing chains of molecules (41) may be attached within the pores, thus amplifying the synthesis by the additional surface area available beneath the surface of the substrate.

Figure 2:
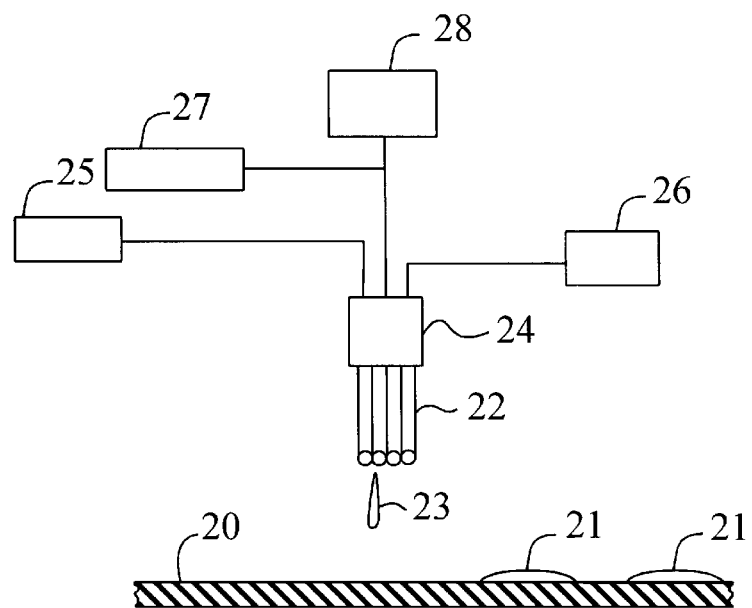
FIG. 2 is a schematic side view of a microdrop dispenser and substrate.

Referring to FIG. 2 there is shown a schematic elevation of the substrate 20 upon which is located on one surface thereof the microdrops 21. Schematically shown is the microdrop multiple jet head dispenser 22 from which, as shown, is being dispensed a microdrop 23. The microdrop is dispensed by a pressure pulse generating means 24, such as a piezoceramic driven pressure pulse device as is typically known in the art of inkjet printers. The timing and amplitude of the pulse are controlled by a suitable electrical controller 25. The location of the dispenser 22 may be suitably controlled by a computer controlled mechanical grid or arm by which precise movements of the dispenser to different locations over the surface 20 can be controlled by control means 26. A reagent source 28 may serve as a reservoir for a particular reagent which is being dispensed, with the flow of the reagent being controlled by a flow controller 27. Alternatively, the dispenser 22 may be held stationary and the substrate 20 may be moved by appropriate controllers in a precise way to locate the microdrops on the substrate surface 20. As part of the control of the location of the dispenser 22, the controlling means 26 will also contain a memory to record the identity of each reagent and the sequence at which they were added to each microdrop locus.

Figure 3:
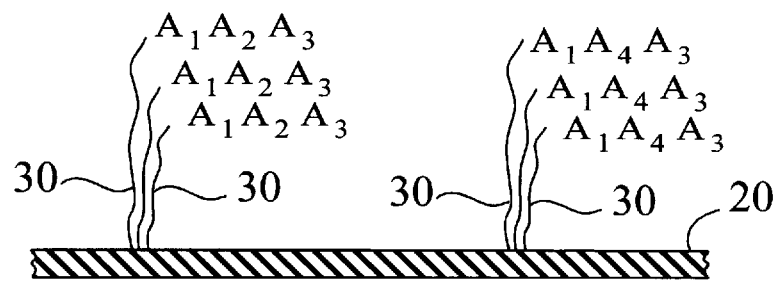
FIG. 3 is a schematic illustration of two loci at which different peptides are prepared.

Referring to FIG. 3, there is shown an elevational view of the substrate 20 and a schematic view of the elements which may be present at two of the microdrop loci. At each of the loci there is a plurality of chemical linkers 30 which are attached at one end to the substrate surface 20 and at the other end to a molecule which is being synthesized at the particular locus. In the figure the letter "A" represents an amino acid. By separate microdrop treatments in one locus the peptide having the sequence (using conventional peptide nomenclature whereby the last amino acid added to the chain is the N-terminus) the peptide $A_3A_2A_1$ has been made by applying in sequence the reagents containing the amino acids $A_1$, $A_2$ and $A_3$. At the other microdrop location the peptide $A_3A_4A_1$ has been made by applying in sequence the amino acid reagents containing $A_1$, $A_4$ and $A_3$.

Figure 4:
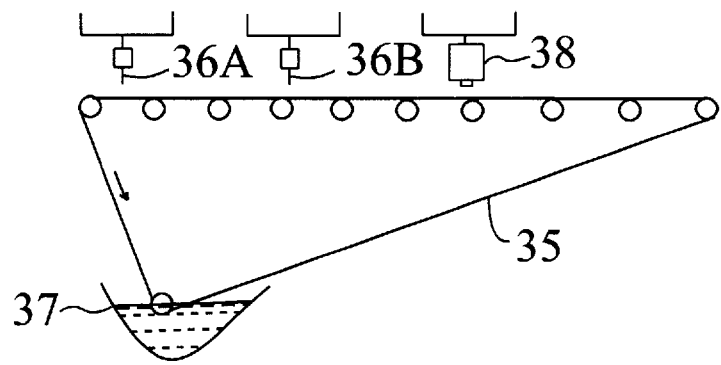
FIG. 4 is a schematic illustration of a flexible, continuous substrate used with the method of the invention.

Referring to FIG. 4, there is shown a schematic diagram of one embodiment of an apparatus utilizing the present invention. The substrate 35 is a continuous, flexible material to which chemicals may covalently linked, such as flexible polystyrene having surface groups to which chemical linkers may be attached, such as those used in solid phase peptide synthesis. One or more electromechanically controlled dispensers 36A and 36B are used to apply microdrops onto the substrate 35. The movement of the substrate 35 is also electromechanically controlled in the longitudinal direction shown by the arrow. The movement of the dispensers 36A and 36B may be controlled along the transverse direction, as well as along the longitudinal direction. Excess reagent is washed off in a bath in tank 37. Detecting means 38, which is also controlled in the transverse and lateral directions, is utilized to observe the loci for either quality control or, in the case of a diagnostic use, for a signal such as fluorescence, radioactivity, polarization, chemiluminescence, etc.

EXAMPLE 1

Ink Jet Device

A device for reagent delivery was constructed consisting of two 25 mm micrometers that provide x and y translation coupled to 10 V, 0.5 amp per phase, 200 step per revolution stepper motors. A single motor step gives a travel of 2.5 $\mu$m. A 48 V power supply with dropping resistors was incorporated to increase high speed motor torque. A piezoelectric ink jet head was mounted vertically to a third 12.5 mm micrometer. The jet was positioned to fire droplets upwards to the underside of a microscope slide held to the top of a platform with a spring loaded slide holder. Electric pulses were generated with electronics that allow all pulse parameters, such as the driving voltage, pulse duration and frequency, to be adjusted. A video camera, which translates in x and y with the jet, was positioned above the slide to monitor drop ejection by focusing on the lower slide surface. Alternately, the camera could be rotated to view across the jet nozzle with lighting provided by a strobed LED to allow for visualization of ejected droplets.

The ink-jet device was controlled by C/C++ program ASyn, with a Windows interface incorporated such that nearly all functions can be done with a mouse which can be placed inside a glove box along with the ink jet device. Asyn provides TTL level triggering to peripheral hardware through a multi-parallel port add-in card on a PC compatible computer.

The software allows for several modes of operation including a manual move and fire, a drawing mode that 'prints' a bitmap image, and a macro execution mode that can 'print' a number of images at different locations. A bitmap is a numerical representation of a two dimensional image made up of an array of pixels. In the case of black and white image, a 1 in the bitmap produces one color while a 0 produces the other. Thus the four bytes FF, 0, FF, and 0, whose binary 'bitwise' representation is 11111111, 00000000, 11111111, and 00000000 would produce alternating white and black lines 8 pixels wide if rendered on a computer screen as a bitmap. The logic of the program divides the arrays into 'addresses' and 'guard' positions that can have variable dimensions. The decision to fire at a given address is determined by the value of a pixel in the bitmap image. The mode of firing at an address can also be controlled to give single or multiple droplets in the center of the address as well as a pattern of single droplets to fill a square address area. In addition, logic has been incorporated into ASyn to generate the appropriate bitmaps for the synthesis of combinatorial arrays of oligonucleotides.

A variety of organic solvents including dibromomethane, nitromethane, acetonitrile and dimethyl formamide were found to be suitable for ink jet delivery. Dichloromethane was not found to be suitable for room temperature delivery although a cooled jet assembly provided better results. A reagent consisting of 0.8M $ZnBr_2$ in 9:1 nitromethane:isopropanol has been selected for the deprotection of the 5'O dimethoxytrityl protected deoxyribose during the on-chip synthesis of oligonucleotides.

While delivering water, the ink-jet pulse parameters can be readily adjusted for the delivery of single droplets free of satellites. When the jet nozzle to microscope slide separation is greater than 100 microns, the drop footprint on a glycidoxypropyl silanized slide can be varied from −150 to −250 microns depending on the driving voltage. When the nozzle to slide separation is less than 60 microns, the footprint is seen to decrease to between 60 and 80 microns. In this case the footprint is relatively independent of the driving voltage.

The driving pulse for the ink jet is optimized by setting the video camera to view across the nozzle of the jet with the LED strobe in the background. Driving voltage and delay parameters are adjusted while firing a continuous stream of droplets. It was found that the deprotecting reagent required a driving voltage that was approximately one third that which was required for water. A high degree of control can be exerted on the droplet size when firing deprotection reagent by adjusting the driving voltage. In the case of firing single droplets onto a slide, the size of the 'footprint' of the droplet as it spread onto the slide surface could be varied from less than 100 $\mu$m to more than 250 $\mu$m by varying the drive voltage. A combination of suitable driving voltage in close positioning has yielded the delivery of droplets of deprotecting agent with a footprint on the order of 60 microns.

EXAMPLE 2

Oligonucleotide Synthesis

Oligonucleotide synthesis was performed using the ink jet to deliver deprotecting reagent.

A standard microscope slide was coated with glycidoxypropyl silane and reacted with tetraethylene glycol. A standard phosphoramidite synthetic cycle was used. The entire synthesis was performed in a dry nitrogen filled glove box. Prior to the first coupling reaction the slide was rinsed with acetonitrile (MeCN, distilled from calcium hydride) and dichoromethane (DCM) and vacuum dried for one minute. Phosphoramidite monomers were dissolved at 0.1M in acetonitrile. Tetrazole was dissolved at 0.5M in MeCN. Coupling was performed by adding 80 $\mu$l each of the tetrazole and phosphoramidite to an aluminum reaction trough. The glass slide was placed into the trough causing the liquid to spread evenly over the slide surface. Reaction was allowed to proceed for three minutes. The slide was then rinsed with MeCN and the coupling procedure repeated.

After coupling, the slide was dipped for two minutes into a Teflon and glass chamber that contained an oxidizing iodine/lutidine/MeCN/water solution purchased from Pharmacia (250 $\mu$l each of Oxidation 1 and Oxidation 2). The slide was then rinsed twice with MeCN and DCM and dried in vacuum.

After drying, the slide was placed onto the ink jet platform for spraying of the appropriate pattern of deprotection reagent. The slide was allowed to sit for a period of five minutes after that last droplet was delivered. The slide was then rinsed twice with MeCN and DCM and vacuum dried in preparation for the next coupling cycle.

A the end of synthesis the slide was removed from the glove box and immersed overnight in a bath of 30% ammonia at room temperature.

A test of simple oligonucleotide synthesis was performed to generate 4×5 arrays of poly-T. In this study, 17 cycles of coupling were performed using a single spray pattern that deposited 15 droplets to all addresses. The addresses were spaced on 2 mm centers. At the end of synthesis the oligonucleotides were deblocked and hybridized with an end-labeled 15-mer of poly-A using 6× SSC/0.5% SDS and 400 ng of end-labeled probe. The synthesis of arrays of poly-T was successful.

It will be appreciated that the above described is intended to be illustrative and not restrictive and that many embodiments will be apparent to those with skill in the art upon reviewing the above description and following claims. The scope of the invention should, therefore, be determined not with reference to the above description, but should instead be determined with reference to the appended claims along with the full scope of equivalents to which such claims are entitled.

What is claimed is:

1. A method of preparing a substrate having a plurality of non-contiguous microdrop-sized loci on a surface of said substrate, wherein said substrate is comprised of a porous material, comprised of a sheet having internal straight, essentially parallel pores and wherein at each of said loci a compound is covalently attached to or beneath said surface, comprising the steps of:
   (a) applying through a single reagent dispenser to a first locus of said surface at least one microdrop of a first liquid activating reagent wherein said reagent modifies said surface at said first locus to activate said surface for forming covalent bonds;
   (b) displacing said single reagent dispenser relative to said surface and applying at least one microdrop of said first activating reagent to said surface at a second locus;
   (c) optionally repeating step (b) at third and subsequent loci, each such locus thereby becoming a modified locus;
   (d) washing the substrate to remove excess reagent;
   (e) applying a quantity of a second reagent to the entire substrate, including loci modified by steps a, b and c to yield the second reagent covalently bound to said surface at said modified loci; and
   (f) repeating step (e) with the same or a different second reagent where the same or different loci have been modified in accordance with steps (a) through (d) until the synthesis of different compounds at each of at least 20 loci is completed.

2. The method of claim 1 wherein said porous material is paper.

3. The method of claim 1 wherein said first activating reagent is a deprotection reagent which removes protecting groups of said locus.

4. The method of claim 1 wherein said first activating reagent is an activation reagent which activates reactive groups of said locus.

5. A method of preparing a substrate having a plurality of non-contiguous microdrop-sized loci on a surface of said substrate, wherein said substrate is comprised a porous material, comprised of a sheet having internal straight, essentially parallel pores and wherein at each of said loci a compound is covalently attached to or beneath said surface, comprising the steps of:
   (a) applying through a single reagent dispenser to a first locus of said surface at least one microdrop of a first liquid activating reagent wherein said reagent modifies said surface at said first locus to activate said surface for forming covalent bonds;
   (b) displacing said single reagent dispenser relative to said surface and applying at least one microdrop of said first activating reagent to said surface at a second locus;
   (c) optionally repeating step (b) at a third and subsequent loci, each such locus thereby becoming a modified locus;
   (d) washing the substrate to remove excess reagent;
   (e) applying a quantity of a second reagent to the entire substrate, including loci modified by steps a, b and c, wherein said second reagent comprises protected or unprotected amino acids, thereby forming polypeptides covalently attached to said surface at said modified loci; and
   (f) repeating step (e) with the same the same or a different second reagent where the same or different loci have been modified in accordance with steps (a) through (c) until the synthesis of polypeptides at each of at least 20 said loci is completed.

6. The method of claim 5 wherein said first activating reagent is a deprotection reagent which removes protecting groups of said locus.

7. The method of claim 5 wherein said first activating reagent is an activation reagent which activates reactive groups of said locus.

8. The method of claim 5 wherein said porous material comprises paper.

9. A method of preparing a substrate having a plurality of non-contiguous microdrop-sized loci on a surface of said substrate, wherein said substrate is comprised of a porous material, wherein said substrate is comprised a porous material, comprised of a sheet having internal straight, essentially parallel pores and wherein at each of said loci a compound is covalently attached to or beneath said surface, comprising the steps of:
   (a) applying through a single reagent dispenser to a first locus of said surface at least one microdrop of a first liquid activating reagent wherein said reagent modifies said surface at said first locus to activate said surface for forming covalent bonds;
   (b) displacing said single reagent dispenser relative to said surface and applying at least one microdrop of said first activating reagent to said surface at a second locus;
   (c) optionally repeating step (b) at third and subsequent loci, each such locus thereby becoming a modified locus;
   (d) washing the substrate to remove excess reagent;
   (e) applying a quantity of a second reagent to the entire substrate, including loci modified by steps a, b and c, wherein said second reagent comprises protected or unprotected nucleotides, thereby forming oligonucleotides covalently attached to said surface at said modified loci; and
   (f) repeating step (e) with the same the same or a different second reagent where the same or different loci have been modified in accordance with steps (a) through (c) until the synthesis of oligonucleotides at each of at least 20 said loci is completed.

10. The method of claim 9 wherein said porous material is paper.

11. The method of claim 9 wherein said first activating reagent is a deprotection reagent which removes protecting groups of said locus.

12. The method of claim 9 wherein said first activating reagent is an activation reagent which activates reactive groups of said locus.

13. A method of preparing a substrate having a plurality of non-contiguous microdrop-sized loci on a surface of said substrate, wherein said substrate is comprised of a porous material, and wherein at each of said loci a compound is covalently attached to or beneath said surface, comprising the steps of:

(a) applying through a single reagent dispenser to a first locus of said surface at least one microdrop of a first activating reagent of 0.8M zinc bromide in 9:1 nitromethane:isopropanol, wherein said reagent modifies said surface at said first locus to activate said surface for forming covalent bonds;

(b) displacing said single reagent dispenser relative to said surface and applying at least one microdrop of said first activating reagent to said surface at a second locus;

(c) optionally repeating step (b) at third and subsequent loci, each such locus thereby becoming a modified locus;

(d) washing the substrate to remove excess reagent;

(e) applying a quantity of a second reagent to the entire substrate, including loci modified by steps a, b and c, wherein said second reagent comprises protected or unprotected nucleotides, thereby forming oligonucleotides covalently attached to said surface at said modified loci; and (f) repeating step (e) with the same the same or a different second reagent where the same or different loci have been modified in accordance with steps (a) through (c) until the synthesis of oligonucleotides at each of at least 20 said loci is completed.

14. A method of preparing a substrate having a plurality of non-contiguous microdrop-sized loci on a surface of said substrate, wherein said substrate is comprised a porous material, comprised of a sheet having internal straight, essentially parallel pores and wherein at each of said loci a compound is covalently attached to or beneath said surface, comprising the steps of:

(a) applying by a pulse through a piezoelectric jet head single reagent dispenser, to a first locus of said surface a quantity of a first liquid activating reagent wherein said reagent modifies said surface at said first locus to activate said surface for forming covalent bonds;

(b) displacing said single reagent dispenser relative to said surface and applying a quantity of said first activating reagent to said surface at a second locus;

(c) optionally repeating step (b) at a third and subsequent loci, each such locus thereby becoming a modified locus;

(d) washing the substrate to remove excess reagent;

(e) applying a quantity of a second reagent to the entire substrate, including loci modified by steps a, b and c, wherein said second reagent comprises protected or unprotected amino acids, thereby forming polypeptides covalently attached to said surface at said modified loci; and (f) repeating step (e) with the same the same or a different second reagent where the same or different loci have been modified in accordance with steps (a) through (c) until the synthesis of polypeptides at each of at least 20 said loci is completed.

15. The method of claim 14 wherein said first activating reagent is a deprotection reagent which removes protecting groups of said locus.

16. The method of claim 14 wherein said first activating reagent is an activation reagent which activates reactive groups of said locus.

17. The method of claim 14 wherein said porous material is paper.

18. A method of preparing a substrate having a plurality of non-contiguous microdrop-sized loci on a surface of said substrate, wherein at each of said loci a compound is covalently attached to or beneath said surface, comprising the steps of:

(a) applying by a pulse through a piezoelectric jet head single reagent dispenser to a first locus of said surface a quantity of a first liquid activating reagent wherein said reagent modifies said surface at said first locus to activate said surface for forming covalent bonds, wherein said piezoelectrectric jet head is positioned at a predetermined distance from said substrate, wherein said predetermined distance is less than the separation distance required for free droplet formation, whereby a smaller volume of liquid reagent is delivered to said substrate per microdrop as compared to the volume per microdrop when a droplet is allowed to form before contact with said substrate;

(b) displacing said single reagent dispenser relative to said surface and applying a quantity of said first activating reagent to said surface at a second locus;

(c) optionally repeating step (b) at a third and subsequent loci, each such locus thereby becoming a modified locus;

(d) washing the substrate to remove excess reagent;

(e) applying a quantity of a second reagent to the entire substrate, including loci modified by steps a, b and c, wherein said second reagent comprises protected or unprotected amino acids, thereby forming polypeptides covalently attached to said surface at said modified loci; and (f) repeating step (e) with the same the same or a different second reagent where the same or different loci have been modified in accordance with steps (a) through (c) until the synthesis of polypeptides at each of at least 20 said loci is completed.

* * * * *